United States Patent [19]

Katsimbas

[11] 4,039,627

[45] Aug. 2, 1977

[54] HEAT-CURABLE PULVERULENT COATING AGENT OF A MIXTURE OF A COPOLYMER CONTAINING GLYCIDYL GROUPS AND AN ADDUCT OF ALIPHATIC DICARBOXYLIC ACID AND 2,4,6-TRIS-(N',N",N'"-DIME-THYLAMINOMETHYL)-PHENOL

[75] Inventor: Themistoklis Katsimbas, Hamburg, Germany

[73] Assignee: Hoechst Aktiengesellschaft, Germany

[21] Appl. No.: 551,126

[22] Filed: Feb. 19, 1975

[30] Foreign Application Priority Data

Feb. 22, 1974 Switzerland .................. 2515/74

[51] Int. Cl.² .......................................... C08L 63/00
[52] U.S. Cl. .................................. 260/836; 260/9;
 260/37 EP; 260/830 R; 260/830 TN; 260/835;
 260/837 R; 427/27; 428/418; 428/461;
 428/462; 526/273

[58] Field of Search .............. 260/836, 837; 106/287;
 428/418, 461; 427/195; 526/273

[56] References Cited

U.S. PATENT DOCUMENTS

| 3,730,930 | 5/1973 | Labana | 260/23 EP |
|---|---|---|---|
| 3,752,870 | 8/1973 | Labana | 260/836 |
| 3,781,379 | 12/1973 | Theodore | 260/836 |
| 3,781,380 | 12/1973 | Labana et al. | 260/836 |
| 3,787,521 | 1/1974 | Labana et al. | 260/836 |
| 3,842,035 | 10/1974 | Klaren | 260/47 EN |
| 3,876,587 | 4/1975 | Matsui | 260/78.4 D |
| 3,925,507 | 12/1975 | Katsimbas | 260/836 |

*Primary Examiner*—Theodore E. Pertilla
*Attorney, Agent, or Firm*—Gordon W. Hueschen

[57] ABSTRACT

The invention relates to heat-curable, pulverulent coating agents, frequently also referred to as powder lacquers, which can be used to apply a coherent coating having excellent properties after heat-curing. The coating agent contains a specifically selected acrylic resin and a specific curing agent.

13 Claims, No Drawings

HEAT-CURABLE PULVERULENT COATING AGENT OF A MIXTURE OF A COPOLYMER CONTAINING GLYCIDYL GROUPS AND AN ADDUCT OF ALIPHATIC DICARBOXYLIC ACID AND 2,4,6-TRIS-(N',N'',N'''-DIMETHYLAMINOMETHYL)-PHENOL

BACKGROUND OF THE INVENTION

It is already known to manufacture, and use, heat curable pulverulent coating agents based on copolymers which contain glycidyl groups. However, such known products have the disadvantage that they have to be stoved at temperatures about 200° C to give resistant films.

If attempts are made to lower the stoving temperatures of such known pulverulent coating agents by addition of accelerators, the effect is inadequate or the films obtained yellow already during the stoving process; at times, the adhesion is also impaired.

Such known powder coating agents are described in German Published Specification Nos. 2,240,312, 2,240,314, 2,240,315, 2,057,577, 2,064,916, 2,214,650 and 2,122,313.

1. It is the object of the present invention to provide a heat-curable, pulverulent coating agent which simultaneously shows improvements in various directions compared to the known pulverulent coating agents. One aim is that it should be possible to manufacture the pulverulent agent by simple mixing, homogenising fusion and conjoint grinding of the requisite components.

2. The pulverulent coating agent manufactured by intensive mixing, homogenising fusion and grinding should be stable on storage at the customary storage temperatures of between about −40 to +40° C.

3. The coating agent should, after application, given very glossy non-yellowing coatings, with good levelling properties and freedom from blisters and craters, merely by stoving at about 150° to 180° C for about 15 to 30 minutes.

4. The stoved films should not yellow and should show excellent weathering resistance and substantially improved resistance to organic solvents and chemicals, the comparison being relative to powder lacquers based on acrylate copolymers.

SUMMARY

The subject of the invention is a pulverulent coating agent of a mixture of

A. a copolymer which contains glycidyl groups and which is a copolymer of several ethylenically unsaturated compounds and has a relatively low molecular weight, B. at least one aliphatic dicarboxylic acid, in an amount corresponding to 0.8 − 1.1 acid groups per epoxy group of the copolymer and C. a curing accelerator in the form of an organic base, and optionally D. a flow control agent, in an amount of at least 0.05 percent by weight of the mixture, which is a polymer of molecular weight ($\overline{M}_n$) at least 1,000 and has a glass transition temperature which is at least 50° C lower than the glass transition temperature of the copolymer (A) characterised in that the component A. consists of 80 to 96 percent by weight of copolymers, containing epoxide groups and hydroxyl groups, which have Durran softening points of about 90° − 120° C and are soluble in organic solvents, of a. 6 to 24 percent by weight of ethylenically unsaturated epoxide monomers with 6 − 12 carbon atoms, of the general formula

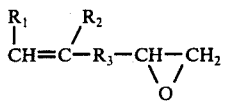

wherein $R_1$ and $R_2$ = H or —$CH_3$ $R_3$ = —C(=O)—O—$CH_2$   or   —$CH_2$—O—$CH_2$   or —$CH_2$—O—C(=O)—CH=CH—C(=O)—O—$CH_2$   or —$CH_2$—O—C(=O)—C$_6$H$_4$—C(=O)—O—$CH_2$—   or is absent b. 4 − 20 percent by weight of hydroxyalkyl esters of acrylic acid or methacrylic acid, wherein the hydroxyalkyl ester group is saturated and contains 2 − 4 carbon atoms c. 10 − 80 percent by weight of acrylic acid esters or methacrylic acid esters of aliphatic saturated monoalcohols with 1 − 8 carbon atoms and d. 10 − 60 percent by weight of styrene or vinyltoluene; and

B. consists of 4 − 20 percent by weight of an adduct of a saturated straight-chain aliphatic dicaboxylic acid of the formula HOOC—(CH$_2$)$_n$—COOH, wherein $n$ is a whole number from 4 to 11, and 2,4,6-tris(N',N'',N'''-dimethylaminomethyl)-phenol, and these components of the adduct can be present in a weight ratio of 97 : 3 to 99 : 1; optionally together with C. other customary additives.

In a preferred embodiment of the invention component A consists of a copolymer, constructed of:
a. 12 to 16 percent by weight of gylcidyl methacrylate,
b. 14 to 18 percent by weight of hydroxyethyl methacrylate,
c. 15 to 25 percent by weight of n-butyl acrylate and 5 to 35 percent by weight of methyl methacrylate and
d. 20 to 50 percent by weight of styrene.

In a further preferred embodiment of the invention component A consists of a copolymer, constructed of:
a. 14 to 22 percent by weight of glycidyl methacrylate,
b. 4 to 12 percent by weight of hydroxyethyl methacrylate,
c. 35 to 50 percent by weight of methyl methacrylate and 6 to 12 percent by weight of 2-ethylhexyl acrylate and
d. 25 to 35 percent by weight of styrene.

In a further preferred embodiment of the invention component A consists of a copolymer, constructed of:
a. 14 to 22 percent by weight of glycidyl methacrylate, b. 4 to 12 percent by weight of hydroxyethyl methacrylate,
c. 30 to 40 percent by weight of butyl methacrylate,
d. 30 to 52 percent by weight of styrene.

As component (a) it is possible to use ethylenically unsaturated epoxy monomers with 6 – 12 carbon atoms, of the general formula $$\overset{R_1}{\underset{CH=C}{|}}\overset{R_2}{\underset{-R_3-CH-CH_2}{\diagup}}_{\diagdown O \diagup}$$

wherein $R_1$ and $R_2$ = H— or —CH$_3$, $$R_3 = -\underset{\underset{O}{\|}}{C}-O-CH_2- \quad \text{or} \quad -CH_2-O-CH_2- \quad \text{or}$$

$$-CH_2-O-\underset{\underset{O}{\|}}{C}-CH=CH-\underset{\underset{O}{\|}}{C}-O-CH_2-$$

or $$-CH_2-O-\underset{\underset{O}{\|}}{C}-\!\!\!\bigcirc\!\!\!-\underset{\underset{O}{\|}}{C}-O-CH_2-$$

or is absent. These include: glycidyl acrylate, glycidyl methacrylate, allyl glycidyl ether, methallyl glycidyl ether, glycidyl crotonate, vinyl glycidyl ether, allyl glycidyl maleate, allyl glycidyl phthalate and butadiene monoxide.

As component (b) it is possible to use hydroxyalkyl esters of acrylic or methacrylic acid, such as hydroxyethyl acrylate, hydroxyethyl methacrylate, hydroxypropyl acrylate and hydroxybutyl acrylate.

As component (c) it is possible to use acrylic acid esters or methacrylic acid esters of aliphatic saturated monoalcohols with 1 – 8 carbon atoms: methyl methacrylate, ethyl acrylate, butyl acrylate, 2-ethylhexyl acrylate, 2-ethylhexyl methacrylate, isobutyl acrylate and butyl methacrylate. n-Butyl acrylate or n-butyl methacrylate are employed preferentially.

Styrene or vinyltoluene is co-used as component (d).

The copolymers are manufactured according to known processes of bulk polymerisation, solution polymerisation and dispersion polymerisation, preferably by solution polymerisation. Such processes are described, for example, in "Methoden der Organischen Chemie" (Methods of Organic Chemistry), Houben-Weyl, 4th Edition, Volume 14/1, pages 24 to 556 (1961).

If the polymerisation is caried out in solution, it is possible to employ solvents, such as methylene chloride, ethanol, iso-propanol, n-propanol, n-butanol, isobutanol, tert.-butanol, the methyl to bis-butyl esters of acetic acid, acetone, methyl ethyl ketone, benzene, toluene and others.

The polymerisation is carried out at temperatures of 40° to about 160° C.

Examples of initiators which can be employed are percarbonates, peresters, such as tert.-butyl perpivalate or peroctoate, benzoyl peroxide, o-methoxybenzoyl peroxide, dichlorobenzoyl peroxide and azodiisobutyric acid dinitrile, in amounts of 0.5 to 8% by weight, based on monomers.

Furthermore, customary molecular weight regulators, such as n-dodecylmercaptan or tert.-dodecylmercaptan, can be co-used.

The copolymer solution is freed from the solvent by distilling off the latter in vacuo or in suitable apparatuses, preferably vapouriser screws, at temperatures of about 90° to 240° C, and is cooled, granulated and ground. However, the product can also be isolated in accordance with other processes, say by spray drying, removal of the solvent with water vapour and simultaneous dispersion in water, or precipitation with water from a water-miscible solvent.

Dicarboxylic acids which have 4 to 11 carbon atoms in the chain and can be used for the manufacture of the adduct (component B) are adipic acid, pimelic acid, suberic acid, azelaic acid, sebacic acid, decane-1,10-dicarboxylic acid and undecane-1,11-dicarboxylic acid. In general, aliphatic dicarboxylic acids with a melting point in the range from 80° to 160° C are preferred.

It is known to use 2,4,6-tris(N',N'',N'''-dimethylaminomethyl)-phenol as a curing agent (primary curing agent) for epoxide resins. Furthermore, its use in combination with polyaminoamides for the same purpose is known. The addition of catalytic amounts of 2,4,6-tris(N',N'',N'''-dimethylaminomethyl)-phenol has been recommended for epoxide resin coatings which contain a curing agent (compare the bulletin "Curing Agents for Epoxide Resins" of ANCHOR Chemical Company Ltd., Manchester 11, England, page 7 and 8).

However, it was not known, and also not to be expected that this known curing agent, in the form of an adduct with straight-chain aliphatic dicarboxylic acids with 4 to 11 carbon atoms, would exert an accelerating effect on the curing of the epoxide resins by acids, with, surprisingly, no yellowing occurring during or after curing.

As the flow control agent (D) it is possible to use, in the pulverulent coating agent, an acrylic polymer having a glass transition temperature which is at least 50° C lower than the glass transition temperature of the copolymer used in the mixture.

Preferred acrylic polymers which can be used as flow control agents are polylauryl acrylate, polybutyl acrylate, poly(2-ethylhexyl acrylate), polylauryl methacrylate and polyisodecyl methacrylate.

The flow control agent can also be a fluorinated polymer which has a lower surface tension, at the stoving temperature of the powder mixture, than the copolymer used in the mixture. If a fluorinated polymer is used as the flow control agent, esters of polyethylene glycol or polypropylene glycol and fluorinated fatty acids are preferred. An example of a suitable flow control agent is an ester of polyethylene glycol, of molecular weight above 2,500, and perfluoroctanoic acid. Furthermore, levelling agents and other adducts improving the properties, such as silicones, polyesters, ketone resins, epoxide resins and cellulose derivatives, can be added to the melts. It is also possible to add pigments, flow control agents and other additives customary in such coating agents.

The adduct of a saturated straight-chain aliphatic dicarboxylic acid with 4 – 11 carbon atoms in the chain and 2,4,6-tris(N',N'',N'''-dimethylaminomethyl)-phenol is manufactured by fusing the aliphatic dicarboxylic acid under an inert gas, for example nitrogen, and introducing the 2,4,6-tris-(N',N'',N'''-dimethylaminomethyl)-phenol whilst continuing to heat the melt of 5 to 10 minutes, after which the melt is chilled. The temperatures of the melt are approximately between 80° and 160° C. The chilling is carried out, for example, by pouring the adduct melt onto cold metal sheets.

Adducts which can be used may have the following composition: 97 parts by weight of adipic acid and 3 parts by weight of 2,4,6-tris(N',N'',N''',-dimethylaminomethyl)-phenol, 98 parts by weight of adipic acid and 2 parts by weight of 2,4,6-tris(N',N'',N'''dimethylaminomethyl)-phenol, 98.5 parts by weight of adipic acid and 1.5 parts by weight of 2,4,6-tris(N',N'',N'''-dimethylaminomethyl-phenol, 98 parts by weight of pimelic acid and 2 parts by weight of 2,4,6-tris(N',N'',N'''-dimethylaminomethyl)-phenol, 98 parts by weight of suberic acid and 2 parts by weight of 2,4,6-tris(N',N'',N'''-dimethylaminomethyl)-phenol, 98 parts by weight of azelaic acid and 2 parts by weight of 2,4,6-tris-(N',N'',N'''-dimethylaminomethyl)-phenol, 98.5 parts by weight of azelaic acid and 1.5 parts by weight of 2,4,6-tris(N',N'',N'''-dimethylaminomethyl)-phenol, 99 parts by weight of azelaic acid and 1 part by weight of 2,4,6-tris-(N',N'',N'''-dimethylaminomethyl)-phenol, 98 parts by weight of sebacic acid and 2 parts by weight of 2,4,6-tris(N',N'',N'''-dimethylaminomethyl)-phenol, 98.5 parts by weight of sebacic acid and 1.5 parts by weight of 2,4,6-tris(N',N'',N'''-dimethylaminomethyl)-phenol and 97.5 parts by weight of undecane-1,11-dicarboxylic acid and 2.5 parts by weight of 2,4,6-tris(N',N'',N'''-dimethylaminomethyl)-phenol.

Preferred adduct compositions are the following: 98 parts by weight of adipic acid and 2 parts by weight of 2,4,6-tris(N',N'',N'''-dimethylaminomethyl)-phenol, 98.5 parts by weight of adipic acid and 1.5 parts by weight of 2,4,6-tris(N',N'',N'''-dimethylaminomethyl)-phenol, 98 parts by weight of azelaic acid and 2 parts by weight of 2,4,6-tris(N',N'',N'''-dimethylaminomethyl)-phenol and 98 parts by weight of sebacic acid and 2 parts by weight of 2,4,6-tris(N',N'',N'''-dimethylaminomethyl)-phenol.

Especially good results are achieved by an adduct of 97.8 parts by weight decane-1,10-dicarboxylic acid and 2.2 parts by weight of 2,4,6-tris(N',N'',N'''-dimethylaminomethyl)-phenol if excellent good stability on storage of the coating agent ready for use is estimated and if one requires excellent good levelling properties, gloss and adhesion of the cured coatings.

The solvent-free, optionally pigmented components, which are brittle in the non-crosslinked state, are ground to particles of about 100 to 300 μm size, fused at about 95° – 110° C whilst mixing or kneading thoroughly, cooled and, after solidification, again ground to finest particles size.

It is preferred to grind to the finest particle size of 5 to 120 μm. The most preferred range of finest grinding is seen between 5 and 75 μm. Moreover, the grinding products can be obtained by sifting according to particles size.

The pulverulent coating agents to be used according to the invention are still free-flowing at temperatures of at least 30° – 40° C, preferably 40° C, have levelling temperatures of approx. 80° to 120° C and are stoved at temperatures from 140° C to 190° C, preferably 160° to 180° C, at which cross-linking takes place. The stoved films should generally possess a layer thickness of 15 to 80 μm.

The pulverulent coating agent is applied to suitable substrates, especially metals, in accordance with the known methods, for example of the electrostatic powder spraying process.

The stoved films of the pulverulent coating agent used according to the invention have excellent adhesion and hardness coupled with elasticity. Furthermore they are distinguished by high gloss, very good weathering resistance and very good resistance to wash liquors.

The powders can be used for coating household equipment, metal components in automobile manufacture, metal components exposed to weathering factors, such as facade panels, pipes, wire netting, equipment for forestry and agriculture and other metal components for interior design.

The examples which follow described the manufacture of the powders and their use as electrostatically sprayable powders. The parts and percentages mentioned in the examples are by weight, unless stated otherwise.

EXAMPLE 1

490 g of toluene are initially introduced into a two-liter stirred pot equipped with a reflux condenser, thermometer and two dropping funnels. The toluene is brought to the reflux temperature of about 112° C and two monomeric mixtures are added dropwise thereto simultaneously over the course of 4 hours, the mixtures being:

a. 375 g of styrene, 225 g of methyl methacrylate, 250g of butyl acrylate, 200 g of hydroxyethyl methacrylate and 200 g of glycidyl methacrylate and b. 64 g of tert.-butyl peroctoate and 44 g of toluene.

The mixture is then kept under reflux for a further hour and at the same time an addition of 4 g of tert.-butyl peroctoate are added dropwise. Polymerisation is then continued for a further 2 hours under reflux at about 118° – 120° C. The resulting copolymer has a Gardner-Holdt viscosity of Q-R, measured on a 50% strength solution in toluene at 20° C. After adding 2.5 g of a flow control agent (Modaflow of Messrs. Monsanto Chemicals) and distilling off the toluene at temperatues up to 160° C under reduced pressure at 40 mm Hg, a brittle, clear solid resin which can easily be powdered, is obtained.

300 g of the resulting solid resin are ground with 32 g of an adduct consisting of 98% by weight of adipic acid and 2% by weight of 2,4,6-tris(N',N'',N'''-dimethylaminomethyl)-phenol and with 132 g of titanium dioxide (of the rutile type) of particles size about 80–200 μm. The power mixture is then mixed for 4 minutes in an extruder at 100° C and the melt is chilled to room temperature and ground to give particles of approx. 80 μm.

The pulverulent coating agent is applied by means of an electro-spray gun onto degreased phosphatised galvanised steel sheets and then stoved for 30 minutes at 180° C.

Coatings having the following properties are obtained:

| | |
|---|---|
| coating thickness: | 55–60 μm |
| levelling, assessed visually: + | 2 |
| folding test: + | 0–1 |
| yellowing: + | 0–1 |
| xylene resistance, 2 hours: + | 0 |
| pencil hardness: | H5 |
| Erichsen deep-drawing value: | 7.5 mm |

-continued

| | |
|---|---|
| gloss, by the Lange method: | 102 |
| grid cut: + | 0 |

+0 = best value  5 = worst value

EXAMPLE 2

The procedure followed is as in Example 1, except that a copolymer is produced from the following monomer mixture:
600 g of styrene,
250 g of butyl acrylate,
200 g of hydroxyethyl methacrylate and
200 g of glycidyl methacrylate.
The resulting copolymer is converted to a pulverulent coating agent in accordance with the instructions in Example 1.

EXAMPLE 3

490 g of toluene are initially introduced into a two-liter stirred pot equipped with a reflux condenser, thermometer and two dropping funnels. The toluene is brought to reflux temperature of about 112° C and two monomeric mixtures are added dropwise thereto simultaneously over the course of 4 hours, the mixtures being
 a. 375 g of styrene, 325 g of methyl methacrylate, 150 g of 2-ethylhexyl acrylate, 200 g of hydroxyethyl methacrylate, 200 g glycidyl methacrylate
and
 b. 58 g of tert.-butyl peroctoate and 44 g of toluene.
The mixture is then kept under reflux for a further hour and at the same time an addition of 4 g of tert.-butyl peroctoate are added dropwise. Polymerisation is then continued for a further 2 hours under reflux at about 118° to 120° C. The resulting copolymer has a Gardner-Hodt viscosity of O – P, measured on a 50% strength solution in toluene at 20° C. After distilling off the toluene at temperatures up to 160° C under reduced pressure at 40 mm Hg a brittle, clear solid resin which can easily be powdered, is obtained.

300 g of the resulting solid resin are ground with 40 g of an adduct consisting of
 97.8 percent by weight of azelaic acid and
 2.2 percent by weight of 2,4,6-tris(N',N'',N'''-dimethylaminomethyl)-phenol and
 132 g of titanium dioxide (of the rutile type) of particle size about 80 – 200 μm.
The powder mixture is then mixed for 4 minutes in an extruder at 100° C and the melt is chilled to room temperature and ground to give particles of appox. 80 μm.

The pulverulent coating is applied by means of an electro-spray gun onto degreased phosphatised galvanised steel shets and then stoved for 30 minutes at 180° C.

Coatings having the following properties are obtained:

| | |
|---|---|
| coating thickness: | 55–60μm |
| levelling, assessed visually: + | 2 |
| folding test: + | 0 |
| yellowing: + | 0–1 |
| xylene resistance, 2 hours: + | 0 |
| pencil hardness: | H5 |
| Erichsen deep-drawing value: | 8.4 mm |
| gloss, by the Lange method: | 96 |
| grid cut: + | 0 |

+0 = best value  5 = worst value

EXAMPLE 4

490 g of toluene are initially introduced into a two-liter stirred pot equipped with a reflux condenser, thermometer and two dropping funnels. The toluene is brought to reflux temperature of about 112° C and two monomeric mixtures are added dropwise thereto simultaneously over the course of 4 hours, the mixtures being
 a. 475 g of styrene, 365 g of methyl methacrylate, 150 g of 2-ethylhexyl acrylate, 50 g of hydroxyethyl methacrylate, 210 g of glycidyl methacrylate
and
 b. 52 g of tert.-butyl peroctoate and 44 g of toluene.
The mixture is then kept under reflux for a further hour and at the same time an addition of 4 g of tert.-butyl peroctoate are added dropwise. Polymerisation is then continued for a further 2 hours under reflux at about 118° to 120° C. The resulting copolymer has a Gardner-Holdt viscosity of M – N, measured on a 50% strength solution in toluene at 20° C. After distilling off the toluene at temperatures up to 160° C under reduced pressure at 40 mm Hg a brittle, clear solid resin which can easily be powdered, is obtained.

300 g of the resulting solid resin are ground with 40 g of an adduct consisting of
 97.8 percent by weight of azelaic acid and
 2.2 percent by weight of 2,4,6-tris(N',N'', N'''-dimethylaminomethyl)-phenol and
 132 g of titanium dioxide (of the rutile type) of particle size about 80 – 200 μm.
The powder mixture is then mixed for 4 minutes in an extruder at 100° C and the melt is chilled to room temperature and ground to give particles of approx. 80 μm.

The pulverulent coating is applied by means of an electro-spray gun onto degreased phosphatised galvanised steel sheets and then stoved for 30 minutes at 180° C.

The resulting coatings are resistant for several hours to alkaline wash liquors up to 80° C.

EXAMPLE 5

270 g of the solid resin obtained according to Example 3 are ground together with 30 g of a epoxy resin (equivalent weight of 1,800 to 2,300), based on bisphenol A and epichlorohydrin, and 40 g of an adduct, consisting of 97.8 percent by weight of azelaic acid and
 2.2 percent by weight of 2,4,6-tris(N',N'',N'''-dimethylaminomethyl)-phenol and
 132 g of titanium dioxide (of the rutile type) of particle size about 80 – 200 μm.
The powder mixture is then mixed for 4 minutes in an extruder at 100° C, and the melt is chilled to room temperature and ground to give particles of approx. 80 μm.

The pulverulent coating is applied by means of an electro-spray gun onto degreased phosphatised galvanised steel sheets and then stoved for 30 minutes at 180° C. The resulting coatings have excellent mechanical and levelling properties.

EXAMPLE 6

The procedure followed is as in Example 1, except that a copolymer is produced from the following monomer mixture:
376 g of styrene,
512 g of methyl methacrylate,
64 g of hydroxyethyl methacrylate,
212 g of glycidyl methacrylate and
86 g of 2-ethylhexyl acrylate.

300 g of the resulting solid resin are ground with 40 g of and adduct consisting of
 97.8 percent by weight of decane-1,10-dicarboxylic acid and
 2.2 percent by weight of 2,4,6-tris(N',N'',N'''-dimethylaminomethyl)-phenol,
132 g of titanium dioxide (of the rutile type) of particle size about 80 – 200 μm and
6 g of an agent for improvement of pigment cross-linking, polyester based (Borchigol VL-73 BK 424, Firma Gebr. Borghers AG, Goslar).

The powder mixture is then mixed for 4 minutes in an extruder at 100° C and the melt is chilled to room temperature and ground to give particles of approx. 80 μm.

The pulverulent coating is applied by means of an electro-spray gun onto degreased phosphatised galvanised steel sheets and then soved for 30 minutes at 180° C.

Coatings having the following properties are obtained:

| | |
|---|---|
| coating thickness: + | 48–55μm |
| levelling, assessed visually: + | 0–1 |
| folding test: + | 0 |
| yellowing: + | 0 |
| xylene resistance, 2 hours: + | 0 |
| pencil hardness: | H5 |
| Erichsen deep-drawing value: | 9.4 mm |
| gloss, by the Lange method: | 104 |
| grid cut: + | 0 |

+0 = best value   5 = worst value

The resulting coating agent shows an excellent stability on storage. The coating films stoved for 30 minutes at 160° – 190° C are distinguished by excellent levelling properties, high gloss and excellent adhesion on meta. substrates.

EXAMPLE 7

The procedure followed is as in Example 1, except that a copolymer is produced from the following monomer mixture:
 500 g of styrene,
 474 g of butyl methacrylate,
 64 g of hydroxyethyl methacrylate and
 212 g of glycidyl methacrylate.

The resulting copolymer is manufactured as pulverulent coating agent according to Example 6.

What is claimed is:
1. Pulverulent coating agent of a mixture of
A. a copolymer which contains glycidyl groups and which is a copolymer of several ethylenically unsaturated compounds and has a relatively low molecular weight,
B. at least one aliphatic dicarboxylic acid, in an amount corresponding to 0.8 – 1.1 acid groups per epoxy group of the copolymer and
C. a curing accelerator in th form of an organic base, and optionally
D. a flow control agent, in an amount of at least 0.05 percent by weight of the mixture, which is a polymer of molecular weight ($\overline{M}_n$) at least 1,000 and has a glass transition temperature which is at least 50° C lower than the glass transition temperature of the copolymer (A) characterised in that the component
A. consists of 80 to 96 percent by weight of copolymers, containing epoxide groups and hydroxyl groups, which have Durran softening points of about 90° – 120° C and are soluble in organic solvents, of a. 6 to 24 percent by weight of ethylenically unsaturated epoxide monomers with 6 – 12 carbon atoms, of the general formula

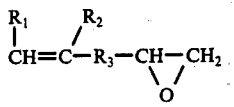

wherein $R_1$ and $R_2$ = H or $-CH_3$ $R_3=$ $-\underset{\underset{O}{\|}}{C}-O-CH_2$ or $-CH_2-O-CH_2$ or $-CH_2-O-\underset{\underset{O}{\|}}{C}-CH=CH-\underset{\underset{O}{\|}}{C}-O-CH_2$ or $-CH_2-O-\underset{\underset{O}{\|}}{C}-\underset{}{\bigcirc}-\underset{\underset{O}{\|}}{C}-O-CH_2-$ or is absent b. 4 – 20 percent by weight of hydroxyalkyl esters of acrylic acid or methacrylic acid, wherein the hydroxyalkyl ester group is saturated and contains 2 – 4 C atoms,
c. 10 – 80 percent by weight of acrylic acid esters or methacrylic acid esters of aliphatic saturated monoalcohols with 1 – 8 carbon atoms and
d. 10 – 60 percent by weight of styrene or vinyltoluene; and
B. consists of 4 – 20 percent by weight of an adduct of a saturated straight-chain aliphatic dicarboxylic acid of the formula $HOOC-(CH_2)_n-COOH$, wherein $n$ is a whole number from 4 to 11, and 2,4,6-tris(N',N'',N'''-dimethylaminomethyl)-phenol, and these components of the adduct can be present in a weight ratio of 97 : 3 to 99:1; optionally together with other customary additives.

2. Pulverulent coating agent according to claim 1 characterised in that the component (A) consists of
a. 12 to 16 percent by weight of glycidyl methacrylate,
b. 14 to 18 percent by weight of hydroxyethyl methacrylate,
c. 15 to 25 percent by weight of n-butyl acrylate and 5 to 35 percent by weight of methyl methacrylate and
d. 20 to 50 percent by weight of styrene.

3. Pulverulent coating agent according to claim 1, characterised in that component (A) consists of
a. 14 to 22 percent by weight of glydicyl methacrylate,
b. 4 to 12 percent by weight of hydroxyethyl methacrylate,
c. 35 to 50 percent by weight of methyl methacrylate and 6 to 12 percent by weight of 2-ethylhexyl acrylate and
d. 25 to 35 percent by weight of styrene.

4. Pulverulent coating agent according to claim 1, characterised in that component (A) consists of
a. 14 to 22 percent by weight of glycidyl methacrylate,
b. 4 to 12 percent by weight of hydroxyethyl methacrylate, c. 30 to 40 percent by weight of butyl methacrylate and d. 30 to 52 percent by weight of styrene.

5. Pulverulent coating agent according to claim 1, characterised in that the copolymer (A) contains polymerised therein, as component (a), ethylenically unsaturated epoxy monomers with 6 – 12 carbon atoms, of the general formula

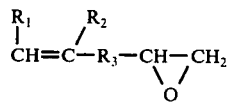

wherein
$R_1$ and $R_2$ = H or —$CH_3$

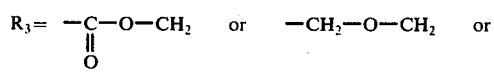

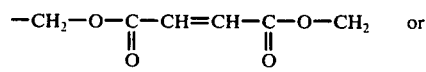

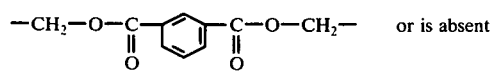

6. Pulverulent coating agent according to claim 1, characterised in that the copolymer (A) contains polymerised therein, as component (b), hydroxyalkyl esters of acrylic acid or methacrylic acid.

7. Pulverulent coating agent according to claim 1, characterised in that the copolymer (A) contains polymerised therein, as component (c), acrylic acid esters or methacrylic acid esters of aliphatic saturated monoalcohols with 1 – 8 carbon atoms.

8. Pulverulent coating agent according to claim 3, characterised in that the component (B) consists of 8 – 12 percent by weight of an adduct, composed of 97.8 parts by weight of decane-1,10-dicarboxylic acid and 2.2 parts by weight of 2,4,6-tris(N',N'',N'''-dimethylaminomethyl)-phenol.

9. Pulverulent coating agent according to claim 1, which is still free-flowing at temperatures of 30° – 40° C, for coating of metal components, preferably in accordance with the electrostatic powder spraying process, and stoving in the range of 140° to 190° C, to obtain very glossy non-yellowing coatings, with good levelling properties and freedom from blisters and craters, excellent weathering resistance and substantially improved resistance to organic solvents and chemicals.

10. A substrate having applied thereto a stoved coating layer in a layer thickness of 15 to 80 μm of a coating agent according to claim 9.

11. Pulverulent coating agent according to claim 5, in which (a) is selected from the group consisting of glycidyl acrylate, glycidyl methacrylate, allyl glycidyl ether, methallyl glycidyl ether, glycidyl crotonate, vinyl glycidyl ether, allyl glycidyl maleate, allyl glycidyl phthalate and butadiene monoxide.

12. Pulverulent coating agent according to claim 6, in which component (b) is selected from the group consisting of hydroxyethyl acrylate, hydroxyethyl methacrylate, hydroxypropyl acrylate and hydroxybutyl acrylate.

13. Pulverulent coating agent according to claim 7, in which component (c) is selected from the group consisting of methyl methacrylate, ethyl acrylate, butyl acrylate, 2-ethylhexyl acrylate, 2-ethylhexyl methacrylate, isobutyl acrylate and butyl methacrylate.

* * * * *

UNITED STATES PATENT OFFICE
CERTIFICATE OF CORRECTION

Patent No. 4,039,627          Dated Aug. 2, 1977

Inventor(s) Katsimbas

It is certified that error appears in the above-identified patent and that said Letters Patent are hereby corrected as shown below:

Col. 5, line 55; "particles" should read ---particle---
Col. 5, line 60; "particles" should read ---particle---
Col. 6, line 16; "described" should read ---describe---
Col. 7, line 37; "Hodt" should read ---Holdt---
Col. 7, line 55; "shets" should read ---sheets---
Col. 8, line 43; "a" should read ---an---
Col. 9, line 17; "sored" should read ---stoved---.
Col. 9, line 33; "meta" should read ---metal---
Col. 9, line 56; "th" should read ---the---

Signed and Sealed this

Second Day of May 1978

[SEAL]

Attest:

RUTH C. MASON
Attesting Officer

LUTRELLE F. PARKER
Acting Commissioner of Patents and Trademarks